United States Patent [19]

Najer et al.

[11] 4,044,132
[45] Aug. 23, 1977

[54] SUBSTITUTED PIPERAZINE DERIVATIVE, ITS PREPARATION AND ANOREXIA COMPOSITIONS CONTAINING IT

[75] Inventors: Henry Najer; Regis Dupont, both of Paris; Don Pierre René Lucien Giudicelli, Fontenay sous Bois, all of France

[73] Assignee: Synthelabo, Paris, France

[21] Appl. No.: 665,884

[22] Filed: Mar. 11, 1976

[30] Foreign Application Priority Data

Mar. 12, 1975 France .................................. 75.07650

[51] Int. Cl.² .................. A61K 31/495; C07D 295/06
[52] U.S. Cl. .............................. 424/250; 260/268 PH
[58] Field of Search .................. 424/250; 260/268 PH

[56] References Cited

U.S. PATENT DOCUMENTS 3,637,705 1/1972 Horrom et al. ............... 260/268 PH

FOREIGN PATENT DOCUMENTS 2,179,491 4/1972 France .......................... 260/268 PH Primary Examiner—Albert T. Meyers
Assistant Examiner—Daren M. Stephens
Attorney, Agent, or Firm—Stevens, Davis, Miller & Mosher

[57] ABSTRACT

The invention provides a new piperazine derivative, 1-(4-fluoro-3-trifluoromethylthio-phenyl)-piperazine of the formula

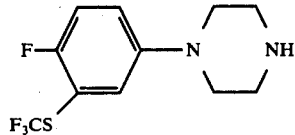

and its pharmaceutically acceptable acid addition salts, which is useful as a medicament in human and veterinary therapy because of its anorexia-inducing effect.

4 Claims, No Drawings

SUBSTITUTED PIPERAZINE DERIVATIVE, ITS PREPARATION AND ANOREXIA COMPOSITIONS CONTAINING IT

This invention relates to substituted piperazine derivatives, their preparation and their use.

The present invention provides the new compound 1-(4-fluoro-3-trifluoromethylthio-phenyl)-piperazine, having the formula (I), and its pharmaceutically acceptable acid addition salts:

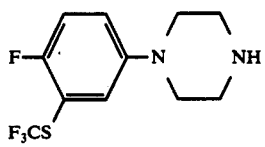
(I)

The compound of formula (I) and its salts can be used in human and veterinary therapy, especially as anorexia-inducing agents.

According to a feature of the invention the compound of formula (I) is prepared by reacting 3-trifluoromethylthio-4-fluoro-aniline with diethanolamine in the presence of a strong acid as catalyst. The compound of formula (I) may be converted into a salt in manner known per se.

This reaction and the reactions by which 3trifluoromethylthio-4-fluoro-aniline may be made are shown in the following reaction scheme.

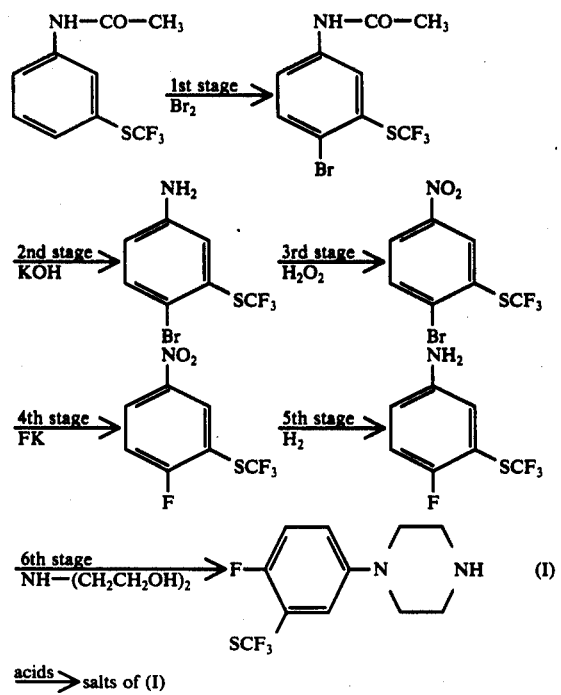

In more detail, these reactions may be effected as follows:

The fixing of bromine to the 3-trifluoromethylthioacetanilide is preferably carried out in a non-polar solvent such as carbon tetrachloride. Two isomers are formed, the bromine becoming fixed in the 4-position or in the 6-position relative to the —NH—CO—CH₃ chain. These two isomers are separated by fractional crystallisation.

The second stage of the reaction is a conventional alkaline hydrolysis. The oxidation of the amine radical to the nitro radical (3rd stage) is advantageously carried out with hydrogen peroxide. Thereafter, the bromine atom is replaced by a fluorine atom by reaction with potassium fluoride at a relatively high temperature (125°–175° C) in a polar solvent such as dimethylsulphoxide (4th stage). The reduction of the nitro derivative to the amine derivative (5th stage) is carried out by catalytic hydrogenation or with another reducing agent and preferably with stannous chloride in hydrochloric acid, under hot conditions.

The final cyclisation to give the piperazine derivative is carried out in a sealed vessel, the reactants being the preceding amine, diethanolamine and an excess of hydrobromic acid (6th stage).

Finally, the salts of the compound (I) may be prepared in manner known per se by treatment of the base with the chosen acid, used in stoichiometric amount or in excess.

The Example which follows illustrates the invention.

EXAMPLE

Synthesis of 1-(4-fluoro-3-trifluoromethylthiophenyl)-piperazine and its hydrochloride (Code number of the hydrochloride: SLC-298)

Stage 1: 3-Trifluoromethylthio-4-bromoacetanilide 100 g (0.425 mol) of 3-trifluoromethylthioacetanilide and 1 liter of anhydrous carbon tetrachloride are introduced into a 2 liter three-neck flask fitted with a condenser, a dropping funnel and a mechanical stirrer. 20 ml of bromine are added dropwise to this mechanically stirred suspension from the dropping funnel. The mixture is left for 1 hour at ambient temperature, while being stirred, and is then heated at the reflux temperature for 2 hours. It is cooled, and ethyl acetate is added until the precipitate formed has dissolved completely. The solution is washed successively with a dilute sodium bisulphite solution and then with water and is dried over sodium sulphate. It is filtered, the solvents are evaporated in vacuo on a water bath, the pasty residue is dissolved in 1,200 ml of a hot 3:2 water-ethanol mixture, the precipitate formed is filtered off while the solution is still lukewarm and is redissoved in 1,100 ml of a hot water-ethanol mixture of the same composition, and the solution is then cooled to 50° C while stirring. The crystals which have separated out are filtered off, washed with alcohol and dried in air.

44 g (32% yield) of 3-trifluoromethylthio-4-bromoacetanilide are thus obtained as a white crystalline compound which melts at 136° C and is chromatographically pure.

Analysis: $C_9H_7BrF_3NOS$ (314); calculated %: C 34.42, H 2.24, Br 25.41, F 18.14, N 4.45; found %: C 34.30, H 2.20, Br 25.03, F 17.92, N 4.43.

The second isomer, 3trifluoromethylthio-6-bromoacetanilide, is isolated from the mother liquors obtained after this fractional crystallisation.

The structure of the isomer retained for the subsequent part of the synthesis was proved after stage 2.

Stage 2: 3-Trifluoromethylthio-4-bromo-aniline 44 g (0.14 mol) of 3-trifluoromethylthio-4-bromoacetanilide, 185 ml of ethanol, 40 ml of water and 40 g (0.7 mol) of potassium hydroxide pellets are introduced into a 1 litre 2-neck flask equipped with a condenser and a mechanical stirrer. This mixture is heated at the reflux temperature, while stirring, for 3 hours, the ethanol is driven off on a water bath in vacuo, the residue is extracted with ethyl acetate, and the organic layer is separated, washed with water and dried over sodium sulphate. It is filtered, the solvents are evaporated from the filtrate in vacuo on a water bath, and the residue is rectified. 36 g (95% yield) of 3-trifluoromethylthio-4-bromo-aniline, b.p. 130° C/8 mm Hg., are thus obtained.

Analysis: $C_7H_5BrF_3NS$ (272); calculated %: C 30.85, H 1.85, Br 29.37, N 5.14; found %: C 30.52, H 1.81, Br 28.96, N 5.25.

Proof of structure: 3-Trifluoromethylthio-4-bromo-aniline is converted, by diazotisation and degradation, to 1-bromo-2-trifluoromethylthio-benzene. The IR and NMR spectra showed that the product was indeed an ortho-disubstituted benzene compound.

Stage 3: 1-Nitro-3-trifluoromethylthio-4-bromo-benzene

A solution of 35 g (0.128 mol) of 3-trifluoromethylthio-4-bromo-aniline in 400 ml of trifluoroacetic acid is heated for 1 hour 30 minutes, at the reflux temperature, in a liter three-neck flask equipped with a condenser, a dropping funnel and a mechanical stirrer. The mixture is allowed to cool and 120 ml of 30% hydrogen peroxide are then added dropwise from the dropping funnel. After the end of the addition, the mixture is heated at the reflux temperature for 2 hours. It is cooled, the contents of the flask are poured into 1.5 liters of ice water, the mixture is left overnight at ambient temperature and extracted with ether, and the ether extract is washed successively with water and with a dilute sodium bicarbonate solution until neutral, and then again with water, and is dried over sodium sulphate. It is filtered, the ether is driven off the filtrate in vacuo on a water bath, and the residue is chromatographed on a column of 1.9 kilograms of silica gel 60, particle size 0.040–0.063 mm, using a 1 : 1 benzene-cyclohexane mixture.

Finally, 23 g (60% yield) of 1-nitro-3-trifluoromethylthio-4-bromo-benzene are obtained as a crystalline compound which melts at 118° C.

Analysis: $C_7H_3BrF_3NO_2S$ (302); calculated %: C 27.84, H 1.00, N 4.64, Br 26.46, F 18.87; found %: C 27.46, H 1.36, N 4.60, Br 18.61.

Stage 4: 1-Nitro-3-trifluoromethylthio-4-fluor-benzene 5.5 g (0.112 mol) of finely divided potassium fluoride are dried by heating at 140° C under a vacuum of 10 mm Hg. in a 100 ml flask for 2 hours. 23 g (0.112 mol) of 1-nitro-3-trifluoromethylthio-4-bromo-benzene and 36 g of anhydrous dimethylsulphoxide are added. This mixture is heated for 15 hours at 150° C while stirring. It is cooled, the contents of the flask are poured into 500 ml of water and extracted with ethyl acetate, and the organic layer is separated, washed with water and dried over sodium sulphate. It is filtered, the solvents are evaporated in vacuo in a water bath and the residue is rectified twice in succession.

Finally, 14 g (yield = 76%) of 1-nitro-3-trifluoromethylthio-4-fluoro-benzene are obtained as a pale yellow liquid which boils at 140°–141° C/8 mm Hg.

Analysis: $C_7H_3F_4NO_2S$ (241); calculated %: C 34.87, H 1.25, N 5.80, F 31.52; found %: C 33.94, H 1.33, N 5.43, F 30.07.

Stage 5: 3-Trifluoromethylthio-4-fluoro-aniline 14 g (0.058 mol) of 1-nitro-3-trifluoromethylthio-4-fluoro-benzene, 36 ml of ethanol and a solution of 65 g of stannous chloride in 43 ml of hydrochloric acid ($d$ = 1.19) are introduced into a 500 ml flask surmounted by a condenser. This mixture is heated at 100° C for 2 hours, the ethanol is evaporated, a large volume of water is added and the mixture is then rendered alkaline with sodium hydroxide solution. It is extracted with ether, the combined ether extracts are washed with water, dried over sodium sulphate and filtered, and the ether is evaporated from the filtrate. The crystalline residue is triturated in a minimum amount of ether and the crystals which have separated out are filtered off.

7 g (60% yield) of 3-trifluoromethylthio-4-fluoro-aniline, m.p. 120° C, are thus obtained.

Analysis: $C_7H_5F_4NS$ (211); calculated %: C 39.81, H 2.38, N 6.63, F 35,98; found %: C 39.41, H 2.38, N 6.48, F 33.07.

Stage 6: 1-(4-Fluoro-3-trifluoromethylthio-phenyl)-piperazine and its hydrochloride 7 g (0.033 mol) of 3-trifluoromethylthio-4-fluoro-aniline and 10.5 g (0.1 mol) of diethanolamine are introduced into a tube which can be sealed. The mixture is homogenised while heating and then saturated with hydrogen bromide gas. The tube is sealed and heated for 15 hours at 200° C. Dilute sodium hydroxide, followed by ethyl acetate, is added to the coloured tarry contents of the tube. A carbonaceous insoluble material is filtered off and washed copiously with ethyl acetate. The organic layer is decanted from the filtrate, washed with water and dried over sodium sulphate. It is filtered, the solvent is evaporated from the filtrate and the highly coloured oily residue is chromatographed on a column of 400 g of silica gel 60, of particle size 0.040–0.063 mm, using a mixture of 10 parts of ethanol-10 parts of acetone-1 part of triethylamine. The solvents are evaporated and the residue is rectified in vacuo. 2.1 g (23% yield) of 1-(4fluoro-3-trifluoromethylthio-phenyl)-piperazine, b.p. 140° C/0.5 mm Hg., are finally obtained.

Its hydrochloride is formed by bubbling a stream of hydrogen chloride gas into a solution of the base in benzene.

Analysis: $C_{11}H_{13}ClF_4N_2S$(316.5); (\*) calculated %: C 40.73, H 4.29, N 8.63, Cl 10.94, F 23,43; found %: C 40.54, H 4.11, N 8.47, Cl 11.34 F 22.39 (\*) theoretical value calculated taking into account a water content of 2.4%, determined by the Karl Fischer method. This hydrochloride melts at 192° C.

The other salts of the base may be prepared in manner known per se by reaction with the appropriate acids used in a stoichiometric amount or in excess.

The compound of the invention was subjected to pharmacological tests which showed its powerful anorexigenic action. Table I below shows the results obtained in comparison with the chosen reference compounds, namely fenfluramine and 1-(4-fluoro-3-trifluoromethyl-phenyl)-piperazine, designated by the code number: SLC-001.

The following methods of study were used:

Acute toxicity: the experiments were carried out on CD1 mice of average weight 20 g. The 50% lethal dose (LD 50) was determined graphically.

Anorexia-inducing action: this property was demonstrated by determining, under rigorously standardised conditions, the amounts of nourishment absorbed by femal SJ (Janvier) rats weighing 180 to 200 g, trained to satisfy their daily food requirements within a period of time limited to 6 hours. The experiment was carried out by administering each compound orally at several doses to batches of 8 animals per dose, 1 hour before the distribution of the food, and graphically determining the 50% active doses (AD 50 = dose capable of reducing the food consumption by 50%).

TABLE I

| Compound under test | Acute toxicity LD 50, mg/kg | | Anorexia-inducing action AD 50, mg/kg, administered orally | |
|---|---|---|---|---|
| | intravenous administration | oral administration | 1st series | 2nd series |
| SLC - 298 (hydrochloride) | 60 | 150 | 1.5 | 1.8 |
| Fenfluramine (hydrochloride) | 42 | 195 | 5 | — |
| SL - 001 (hydrobromide) | 59 | 150 | — | 2.2 |

The AD 50 (i.e. the dose which reduces food consumption by 50% compared with untreated controls) was also determined, in the same way as that described above, on male 'Charles River' rats, 1 hour and 6 hours after administration of the compounds under test. The results obtained are shown in Table II below.

TABLE II

| Compound under test | Anorexia-inducing Action AD 50 mg./kg. orally | |
|---|---|---|
| | after 1 hour | after 6 hours |
| SLC - 298 (hydrochloride) | 1.9 | 2.7 |
| SLC - 001 (hydrobromide) | 2 | >6* |
| dl-Fenfluramine (hydrochloride) | 1.4 | 4 |

*effect between 20 and 40% at the maximum dose tested.

These results show that the compound of the invention is more active than the reference compounds after 6 hours.

It was furthermore confirmed, by a conventional actimetry test carried out on CD1 mice, that SLC-298 only very slightly increases the motility at a low dose (up to 5 mg/kg) while it reduces the motor activity at higher doses (20 mg/kg).

It follows from the above data that the compound SLC-298 is more active as an anorexia-inducing agent than the reference compounds, that its toxicity is moderate, that its therapeutic index is high and that it has little or no stimulant effect.

As a result of all these properties the compound of formula (I), and its addition salts with pharmaceutically acceptable acids, is of therapeutic value, especially for the treatment of various forms of obesity.

The compound of the invention and its salts may be administered by the various usual routes, especially orally, in any suitable pharmaceutical form, such as tablets, dragees, cachets, pills, capsules, potable solutions or potable suspensions, in combination with any suitable excipients. These pharmaceutical compositions can also contain other medicament substances with which the compound (I) and its salts are pharmaceutically and therapeutically compatible.

For oral administration, in particular, the unit dose of compound (I) can vary between 1 and 50 mg, the daily dose being between 4 and 200 mg, in the case of an adult.

The compounds of the invention can also be used as intermediates for the synthesis of other substances.

We claim:

1. 1-(4-Fluoro-3-trifluoromethylthio-phenyl)piperazine of the formula

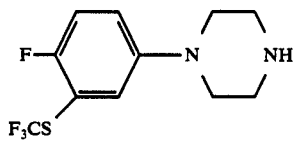

or a pharmaceutically acceptable acid addition salt thereof.

2. The hydrochloride of 1-(4-fluoro-3trifluoro-methylthio-phenyl)-piperazine.

3. An anorexigenic composition comprising a dosage unit form containing 1 to 50 mg of the compound of claim 1 in association with a pharmaceutically compatible carrier or excipient.

4. A method of inducing anorexia in a patient which comprises administering to said patient 1-(4-fluoro-3-trifluoro-methylthio-phenyl)piperazine or a pharmaceutically acceptable salt thereof in an amount sufficient to induce anorexia.

* * * * *